US011350516B2

(12) United States Patent
Bortfeld et al.

(10) Patent No.: US 11,350,516 B2
(45) Date of Patent: *May 31, 2022

(54) SYSTEM AND METHOD FOR GANTRY-LESS PARTICLE THERAPY

(71) Applicant: The General Hospital Corporation, Boston, MA (US)

(72) Inventors: Thomas Bortfeld, Boston, MA (US); Jacob Flanz, Boston, MA (US); Hsiao-Ming Lu, Boston, MA (US); Susu Yan, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/090,809

(22) Filed: Nov. 5, 2020

(65) Prior Publication Data

US 2021/0298162 A1     Sep. 23, 2021

Related U.S. Application Data

(63) Continuation of application No. 16/607,664, filed as application No. PCT/US2018/030791 on May 3, 2018, now Pat. No. 10,880,983.

(Continued)

(51) Int. Cl.
*H05H 7/00*     (2006.01)
*A61N 5/10*     (2006.01)
(Continued)

(52) U.S. Cl.
CPC ........... *H05H 7/001* (2013.01); *A61N 5/1077* (2013.01); *G21K 5/04* (2013.01); *H05H 13/04* (2013.01);
(Continued)

(58) Field of Classification Search
CPC ...... H05H 7/001; H05H 13/04; A61N 5/1077; A61N 5/1078; A61N 2005/1087; A61N 2005/109; G21K 5/04
(Continued)

(56) References Cited

U.S. PATENT DOCUMENTS

| 4,992,746 A | 2/1991 | Martin |
|---|---|---|
| 5,986,274 A | 11/1999 | Akiyama |

(Continued)

FOREIGN PATENT DOCUMENTS

| CN | 102387836 A | 3/2012 |
|---|---|---|
| CN | 102596316 A | 7/2012 |

(Continued)

OTHER PUBLICATIONS

Benedetti, S., et al. "High gradient linac for proton therapy." Physical Review Accelerators and Beams 20.4 (2017): 040101.
(Continued)

*Primary Examiner* — Nicole M Ippolito
(74) *Attorney, Agent, or Firm* — Quarles & Brady LLP (57) ABSTRACT

A gantry-less particle therapy system is provided. Charged particles are extracted from an ion source and accelerated in a beam transport system having an annular portion extending in a first plane and that circumscribes a volume, an arcuate portion extending in a second plane, and a transition portion that connects the annular portion and the arcuate portion. The arcuate portion terminates at a beam nozzle extending radially inward from the annular portion to deliver an ion beam to a treatment area contained in the volume circumscribed by the annular portion.

20 Claims, 7 Drawing Sheets

Related U.S. Application Data (60) Provisional application No. 62/500,668, filed on May 3, 2017.

(51) Int. Cl.
  *G21K 5/04* (2006.01)
  *H05H 13/04* (2006.01)

(52) U.S. Cl.
  CPC ............... *A61N 2005/109* (2013.01); *A61N 2005/1087* (2013.01)

(58) Field of Classification Search
  USPC .......................................... 250/492.1, 492.3
  See application file for complete search history.

(56) References Cited

U.S. PATENT DOCUMENTS

| | | | |
|---|---|---|---|
| 6,803,591 B2 | 10/2004 | Muramatsu | |
| 7,432,516 B2 | 10/2008 | Peggs | |
| 8,766,217 B2 | 7/2014 | Balakin | |
| 10,880,983 B2 * | 12/2020 | Bortfeld ............... | A61N 5/1077 |
| 2007/0201614 A1 | 8/2007 | Goldman | |
| 2009/0309040 A1 | 12/2009 | Balakin | |
| 2010/0054409 A1 | 3/2010 | Bose | |
| 2010/0074392 A1 | 3/2010 | Behling | |
| 2011/0118531 A1 | 5/2011 | Balakin | |
| 2011/0233423 A1 | 9/2011 | Balakin | |
| 2012/0313002 A1 | 12/2012 | Ikeda | |
| 2013/0066134 A1 | 3/2013 | Carol | |
| 2014/0094643 A1 | 4/2014 | Gall | |
| 2015/0190658 A1 | 7/2015 | Yu | |

FOREIGN PATENT DOCUMENTS

| | | |
|---|---|---|
| DE | 4411171 A1 | 10/1995 |
| EP | 2581101 A1 | 4/2013 |
| JP | H08148297 A | 6/1996 |
| JP | 2016115477 A | 6/2016 |
| WO | 2015071430 A1 | 5/2015 |
| WO | 2017212290 A1 | 12/2017 |

OTHER PUBLICATIONS

Betancourt R, et al. SU-E-T-13: A method to improve cone beam CT image quality and Hounsfield units accuracy for prostate proton treatment planning. Med Phys 2011;38:3630.

Bortfeld, T. et al. "Affordable Proton Therapy for Every Patient!" PowerPoint Presentation, Jul. 2017.

Bortfeld, T. R. et al. "Three ways to make proton therapy affordable." Nature News 549.7673 (2017): 451.

Brada M, et al. "Proton therapy: the present and the future." Seminars in radiation oncology. vol. 23. No. 2. 2013. p. 75-76.

Choi S, et al. Comparison of intensity modulated proton therapy (IMPT) to passively scattered proton therapy (PSPT) in the treatment of prostate cancer. Int J Radiat Oncol Biol Phys 2011;81:S154-S155.

Cozzi, L., et al. "A treatment planning comparison of 3D conformal therapy, intensity modulated photon therapy and proton therapy for treatment of advanced head and neck tumours." Radiotherapy and Oncology 61.3 (2001): 287-297.

Das IJ, et al. Proton therapy facility planning from a clinical and operational model. Technol Cancer Res Treat 2015; 14:635-641.

Devicienti S, et al. Patient positioning in the proton radiotherapy era. J Exp Clin Cancer Res 2010;29:1-5.

Engelsman M, et al. Proton radiotherapy: The biological effect of treating alternating subsets of fields for different treatment fractions. Int J Radiat Oncol Biol Phys 2011;79:616-622.

Fattori G, et al. Image guided particle therapy in CNAO room 2: Implementation and clinical validation. Phys Med 2015;31:9-15.

Flanz J, et al. Evolution of technology to optimize the delivery of proton therapy: The third generation. Semin Radiat Oncol 2013;23:142-148.

Goitein M, et al. The relative costs of proton and X-ray radiation therapy. Clin Oncol 2003;15:S37-S50.

Hirao Y, et al. Heavy ion synchrotron for medical use: HIMAC project at NIRS-Japan. Nucl Phys A 1992;538:541-550.

Hsi W, et al. MO-A-213AB-03: Commissioning of a clinical chair for patients treated in the seated position using an inclined beam line treatment room. Med Phys 2012;39:3859.

International Searching Authority, International Search Report and Written Opinion for applicatino PCT/US2018/030791, dated Sep. 17, 2018, 13 pages.

Isacsson U, et al. Potential advantages of protons over conventional radiation beams for paraspinal tumours. Radiother Oncol 1997;45:63-70.

Jermann M. Particle therapy statistics in 2013. Int J Part Ther 2014;1:40-43.

Johnson K, et al. Does respiratory motion change with patient posture? J Nucl Med 2011;52(Suppl. 1):155.

Kang Y, et al. SU-E-T-358: Dosimetric effects of beam angle arrangements in lung proton therapy. Med Phys 2011;38:3570.

Kase Y, et al. A treatment planning comparison of passive-scattering and intensity-modulated proton therapy for typical tumor sites. J Radiat Res 2012;53:272-280.

Lomax AJ, et al. A treatment planning intercomparison of proton and intensity modulated photon radiotherapy. Radiother Oncol 1999;51:257-271.

Lomax AJ, et al. Intensity modulation in radiotherapy: Photons versus protons in the paranasal sinus. Radiother Oncol 2003;66:11-18.

Lu H-M, et al. Proton therapy. In: Paganetti H, editor. Proton therapy physics. New York: CRC Press; 2012. p. 103-156.

MacDonald SM, et al. Proton radiotherapy for pediatric central nervous system germ cell tumors: Early clinical outcomes. Int J Radiat Oncol Biol Phys 2011;79:121-129.

Massachusetts General Hospital. Phase II study of proton beam irradiation for the treatment of unresectable hepatocellular cancer and cholangiocarcinoma. In: ClinicalTrials.gov. Bethesda (MD): National Library of Medicine (US). 2009 [cited Dec. 2014]. Available at: http://clinicaltrials.gov/ct2/show/NCT00976898, NLM Identifier: NCT00976898 Massachusetts General Hospital, 2009 [cited Dec. 2014].

MD Anderson Cancer Center. Intensity-modulated proton beam therapy (IMPT) versus intensity-modulated photon therapy (IMRT). In: ClinicalTrials.gov. Bethesda (MD): National Library of Medicine (US). 2013 [cited Dec. 2014]. Available at: https://clinicaltrials.gov/ct2/show/NCT01893307, NLMIdentifier:NCT01893307.

Miralbell R, et al. Optimizing radiotherapy of orbital and paraorbital tumors: Intensity-modulated X-ray beams vs. intensity-modulated proton beams. Int J Radiat Oncol Biol Phys 2000;47:1111-1119.

PTCOG, Particle Therapy Co-Operative Group. Particle therapy patient statistics (per end of 2013) Available at: http://www.ptcog.ch/index.php/ptcog-patient-statistics.

Radiation Therapy Oncology Group. Comparing photon therapy to proton therapy to treat patients with lung cancer. In: ClinicalTrials.gov. vol. Bethesda (MD): National Library of Medicine (US). 2013 [cited Dec. 2014]. Available from: https://clinicaltrials.gov/ct2/show/NCT01993810, NLM Identifier: NCT01993810, edited by I. ClinicalTrials.gov. Bethesda, MD: National Library of Medicine (US).

Safai S, et al. The rationale for intensity modulated proton therapy in geometrically challenging cases. Phys Med Biol 2013;58:6337-6353.

Sheets NC, et al. Intensity-modulated radiation therapy, proton therapy, or conformal radiation therapy and morbidity and disease control in localized prostate cancer. JAMA 2012;307:1611-1620.

Shinohara, E. Oncolink Module 12: Simulation, Positioning, Verification and Immobilization. Last Reviewed Mar. 18, 2009. Accessed online on Oct. 30, 2019.

Sorensen S, et al. Cone-beam CT using a mobile Carm: A registration solution for IGRT with an optical tracking system. Phys Med Biol 2007;52:3389-3404.

(56) References Cited

OTHER PUBLICATIONS

Suit H, et al. Proton beams to replace photon beams in radical dose treatments. Acta Oncol 2003;42:800-808.

Suzuki K, et al. Quantitative analysis of beam delivery parameters and treatment process time for proton beam therapy. Med Phys 2011;38:4329-4337.

Takazakura R, et al. Diaphragmatic motion in the sitting and supine positions: Healthy subject study using a vertically open magnetic resonance system. J Magn Reson Imaging 2004; 19:605-609.

Tuan J, et al. Initial clinical experience with scanned proton beams at the Italian National Center for Hadrontherapy (CNAO). J Radiat Res 2013;54:i31-i42.

Unkelbach J, et al. Reducing the sensitivity of IMPT treatment plans to setup errors and range uncertainties via probabilistic treatment planning. Med Phys 2009;36:149-163.

Unkelbach J, et al. The emergence of nonuniform spatiotemporal fractionation schemes within the standard BED model. Med Phys 2015;42:2234-2241.

Van De Water, TA, et al. Potential benefits of scanned intensity-modulated proton therapy versus advanced photon therapy with regard to sparing of the salivary glands in oropharyngeal cancer. Int J Radiat Oncol Biol Phys 2011;79:1216-1224.

Van De Water, TA, et al. The potential benefit of radiotherapy with protons in head and neck cancer with respect to normal tissue sparing: A systematic review of literature. Oncologist 2011;16:366-377.

Weber DC, et al. A treatment planning comparison of intensity modulated photon and proton therapy for paraspinal sarcomas. Int J Radiat Oncol Biol Phys 2004;58:1596-1606.

Yan, S., et al. "Reassessment of the necessity of the proton gantry: analysis of beam orientations from 4332 treatments at the Massachusetts General Hospital proton center over the past 10 years." International Journal of Radiation Oncology Biology Physics 95.1 (2016): 224-233.

Yan, S., et al.: Are Proton Gantries Needed? An Analysis of 4332 Patient Proton Gantry Treatment Plans From the Past 10 Years, Poster presentation at the 57th AAPM Annual Meeting, Anaheim, CA, Jul. 12-16, 2015.

Yang J, et al. Advantages of simulating thoracic cancer patients in an upright position. Pract Radiat Oncol 2014;4: e53-e58.

Younkin, J. E., et al. "An efficient daily QA procedure for proton pencil beam scanning." Medical physics 45.3 (2018): 1040-1049.

Zenda S, et al. Proton beam therapy for unresectable malignancies of the nasal cavity and paranasal sinuses. Int J Radiat Oncol Biol Phys 2011;81:1473-1478.

European Patent Office. Extended European Search Report for application 18794458.2, dated Jan. 22, 2021. 10 pages.

China National Intellectual Property Administration. First office action for application 201880036940.2, dated Apr. 27, 2021. With translation. 18 pages.

\* cited by examiner

SYSTEM AND METHOD FOR GANTRY-LESS PARTICLE THERAPY

CROSS-REFERENCES TO RELATED APPLICATIONS

The present application is a U.S. Continuation Application of U.S. patent application Ser. No. 16/607,664 filed Oct. 23, 2019 which represents the national stage entry of PCT International Application No. PCT/US2018/0030791 filed May 3, 2018, which claims priority to U.S. Provisional Patent Application No. 62/500,668, Filed May 3, 2017, entitled "Gantry-less Particle Accelerator," which is hereby incorporated by reference in its entirety.

STATEMENT REGARDING FEDERALLY SPONSORED RESEARCH

Not Applicable.

BACKGROUND

The present disclosure relates, generally, to systems and methods for treating a patient using particle therapy. More specifically, the disclosure relates to systems and methods for treating a patient using particle therapy without the use of a gantry.

Particle therapy systems are currently being used to treat various medical conditions including, for example, several types of cancer. Generally, particle therapy involves directing a beam of energized particles (e.g., protons, neutrons, ions) toward a target tumor. The energized particles then interact with molecules in the cancerous tissue cells within the target tumor, eventually destroying or otherwise damaging the cancerous cells and treating the patient.

Although effective at treating some medical conditions, the cost and space requirements involved with current particle therapy systems have prevented more widespread use. Machines can cost tens of millions of dollars and can require several rooms to house all of the necessary equipment. Due to the space requirements of current particle therapy systems, treatment centers are often required to build new and specialized accommodations for these systems. The financial burden associated with owning a particle therapy system has severely restricted its use.

The type and location of cancerous tissue in a patient can affect where and at what angle particle beams are optimally introduced towards the patient at. Therefore, to create different particle beam orientations, gantries have been used. However, the gantry structures can also be very large and expensive, which has made these treatments inaccessible to many.

To promote more widespread and effective particle therapy solutions, a need exists for a smaller, more cost effective particle therapy system that can provide optimized treatments to individual patients.

BRIEF SUMMARY

The present disclosure provides systems and methods for treating patients using particle therapy that do not require the use of a gantry. The systems and methods disclosed can be used to treat patients in the same room that the particle therapy system is located by positioning the treatment area inward from the beam track of the particle therapy system.

In some aspects, the present disclosure provides a particle therapy system for treating a patient, which includes a charged particle generated system, a beam transport system, and a beam delivery device. The charged particle generating system includes an ion source and an injector that injects an ion beam from the ion source into a beam track. The beam transport system defines the beam track and is coupled to the charged particle generating system. The beam transport system includes a beam tube, a plurality of magnets, and an acceleration cavity. The beam tube is evacuated to a vacuum and includes an energizing segment extending in a first plane and circumscribing a volume to which the ion beam is to be delivered, an extracting segment extending in a second plane that is away from the first plane and terminating at a terminal end, and a transition segment that connects the energizing segment to the extracting segment. The ion beam is received in the energizing segment from the injector. The plurality of magnets adjust a trajectory of the ion beam in the beam tube as the ion beam passes through each of the plurality of magnets, and the acceleration cavity accelerates the ion beam as the ion beam passes through the acceleration cavity.

In some other aspects, the present disclosure provides a particle therapy system for treating a patient. The particle therapy system includes an ion source, an injector that extracts an ion beam from the ion source, a beam tube, and a beam delivery device. The beam tube is coupled to the injector to receive the ion beam from the injector. The beam tube defines a beam track that includes an annular portion formed in a first plane and circumscribing a volume, an arcuate portion formed in a second plane, and a transition portion extending from the first plane to the second plane. The beam delivery device is coupled to the arcuate portion and extends radially inward from the annular portion of the beam track into a patient treatment area contained in the volume circumscribed by the annular portion.

In still other aspects, the present disclosure provides a particle therapy system for treating a patient, which includes a charged particle generation system, a beam transport system, a nozzle, and a patient positioner. The charged particle generating system includes an ion source and an injector that injects an ion beam from the ion source into a beam track. The beam transport system defines the beam track and is coupled to the charged particle generating system. The beam transport system includes a beam tube, a plurality of magnets, and an acceleration cavity. The beam tube is evacuated to a vacuum and includes an energizing segment extending in a first plane and circumscribing a volume to which the ion beam is to be delivered, an extracting segment extending in a second plane that is away from the first plane and terminating at a terminal end, and a transition segment that connects the energizing segment to the extracting segment. The ion beam is received in the energizing segment from the injector. The plurality of magnets adjust a trajectory of the ion beam in the beam tube as the ion beam passes through each of the plurality of magnets, and the acceleration cavity accelerates the ion beam as the ion beam passes through the acceleration cavity. The nozzle is coupled to the terminal end of the extracting segment and is positioned inward from an outer perimeter of the energizing segment. The nozzle includes at least one scanning electromagnet that operates to scan the ion beam over a treatment area in the volume circumscribed by the energizing segment. The patient positioner is received within the treatment area.

In yet another aspect, the present disclosure provides a particle therapy system for treating a patient, which includes an ion source, an injector, a beam tube coupled to the injector, and a beam delivery device. The injector extracts an ion beam from the ion source. The beam tube is coupled to the injector to receive the ion beam from the injector, and defines a beam track. The beam track includes an annular portion circumscribing a volume and an arcuate portion in fluid communication with the annular portion and extending at least partially inward from the annular portion. The beam delivery device is coupled to the arcuate portion and extends radially inward from the annular portion of the beam track into a patient treatment area contained in the volume circumscribed by the annular portion.

The foregoing and other aspects and advantages of the disclosure will appear from the following description. In the description, reference is made to the accompanying drawings which form a part hereof, and in which there is shown by way of illustration a preferred configuration of the disclosure. Such configuration does not necessarily represent the full scope of the disclosure, however, and reference is made therefore to the claims and herein for interpreting the scope of the disclosure.

BRIEF DESCRIPTION OF DRAWINGS

The invention will be better understood and features, aspects and advantages other than those set forth above will become apparent when consideration is given to the following detailed description thereof. Such detailed description makes reference to the following drawings.

Corresponding reference characters indicate corresponding parts throughout the several views. The exemplifications set out herein illustrate embodiments of the invention, and such exemplifications are not to be construed as limiting the scope of the invention in any manner.

DETAILED DESCRIPTION

Generally, the present disclosure provides systems and methods for providing gantry-less particle therapy.

Figure 1:
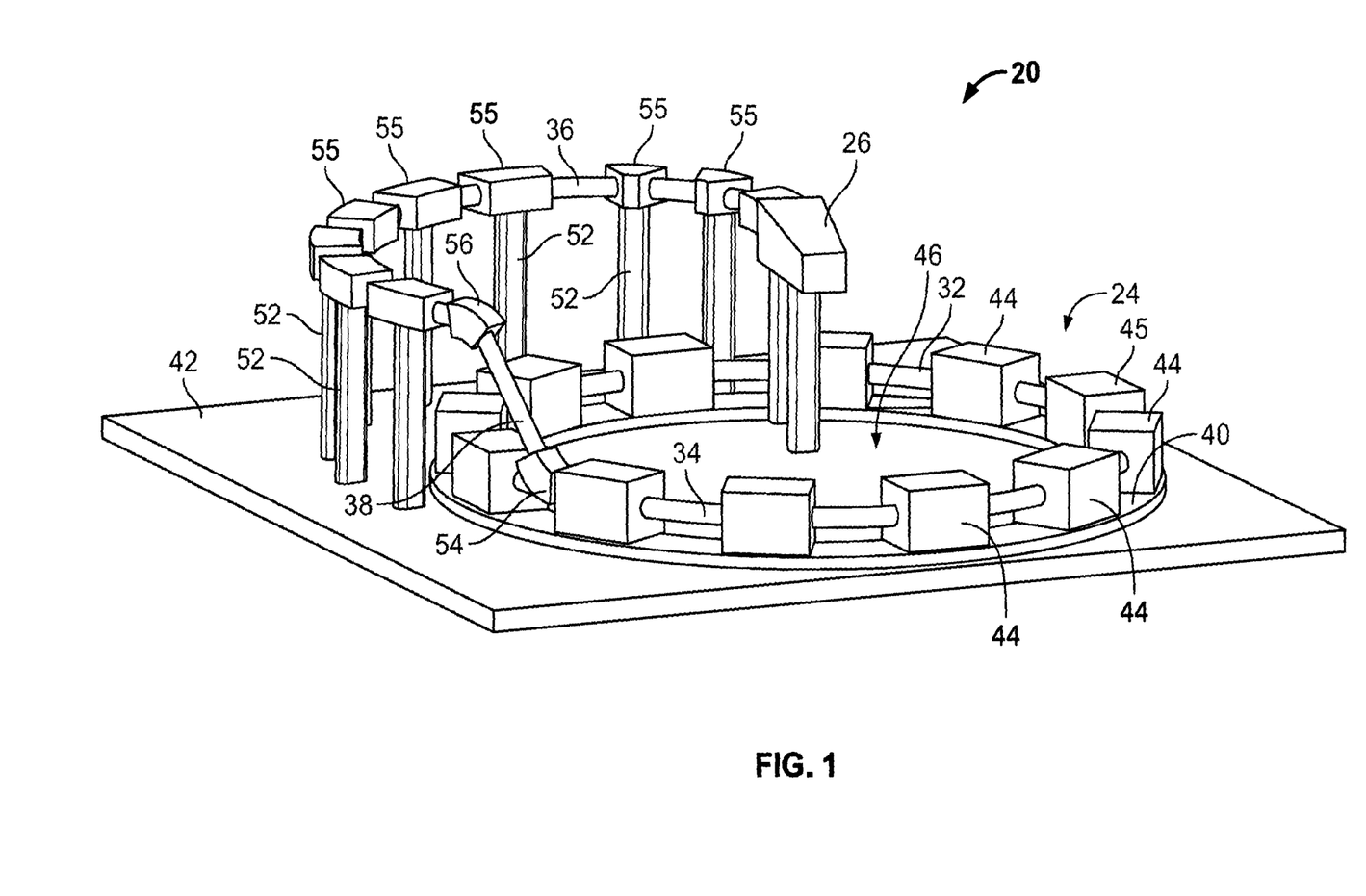
FIG. 1 is a perspective view of one non-limiting example of a particle therapy system according to some embodiments of the present disclosure.
Figure 2:
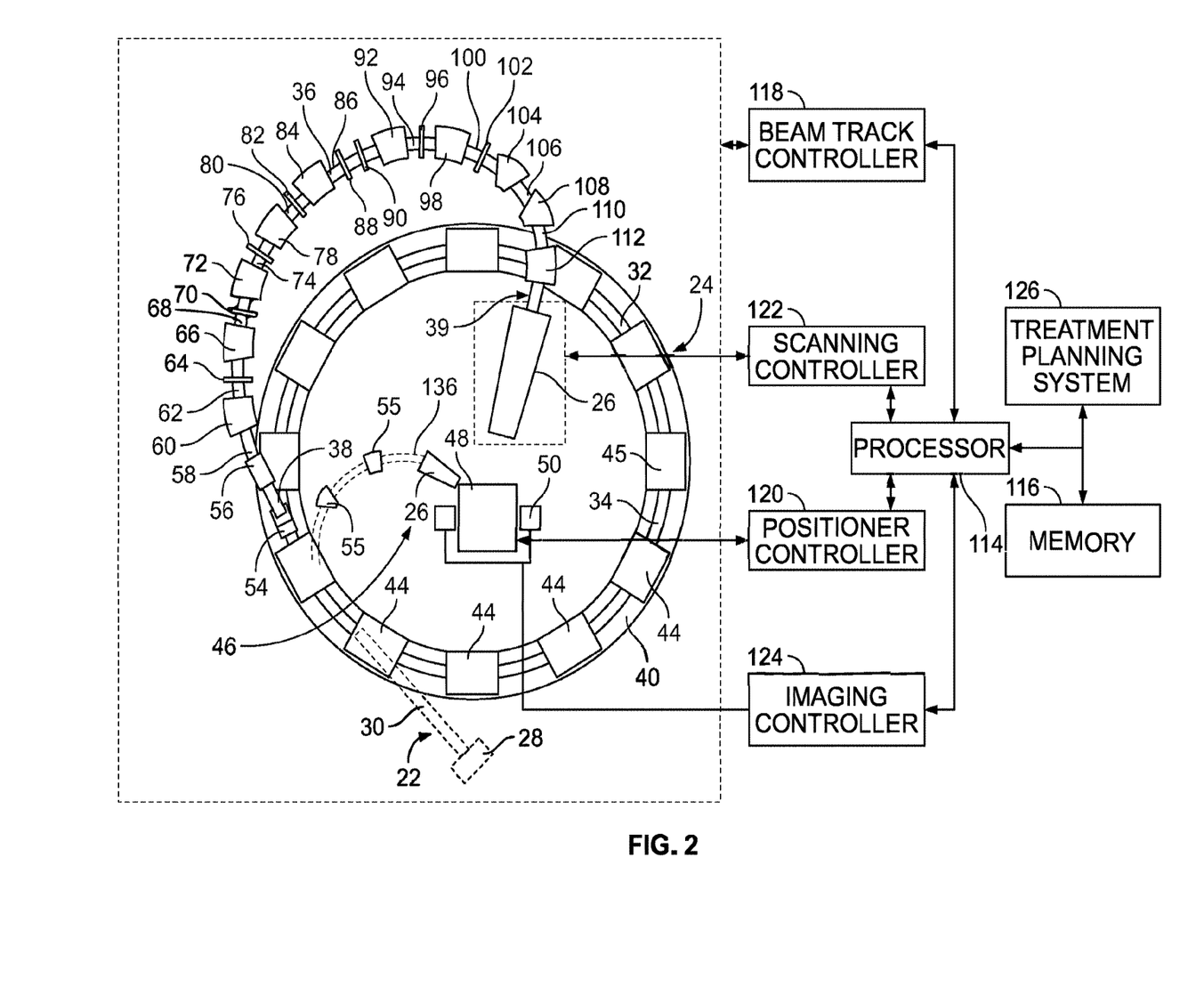
FIG. 2 is a schematic view of the particle therapy system of FIG. 1.
Figure 3:
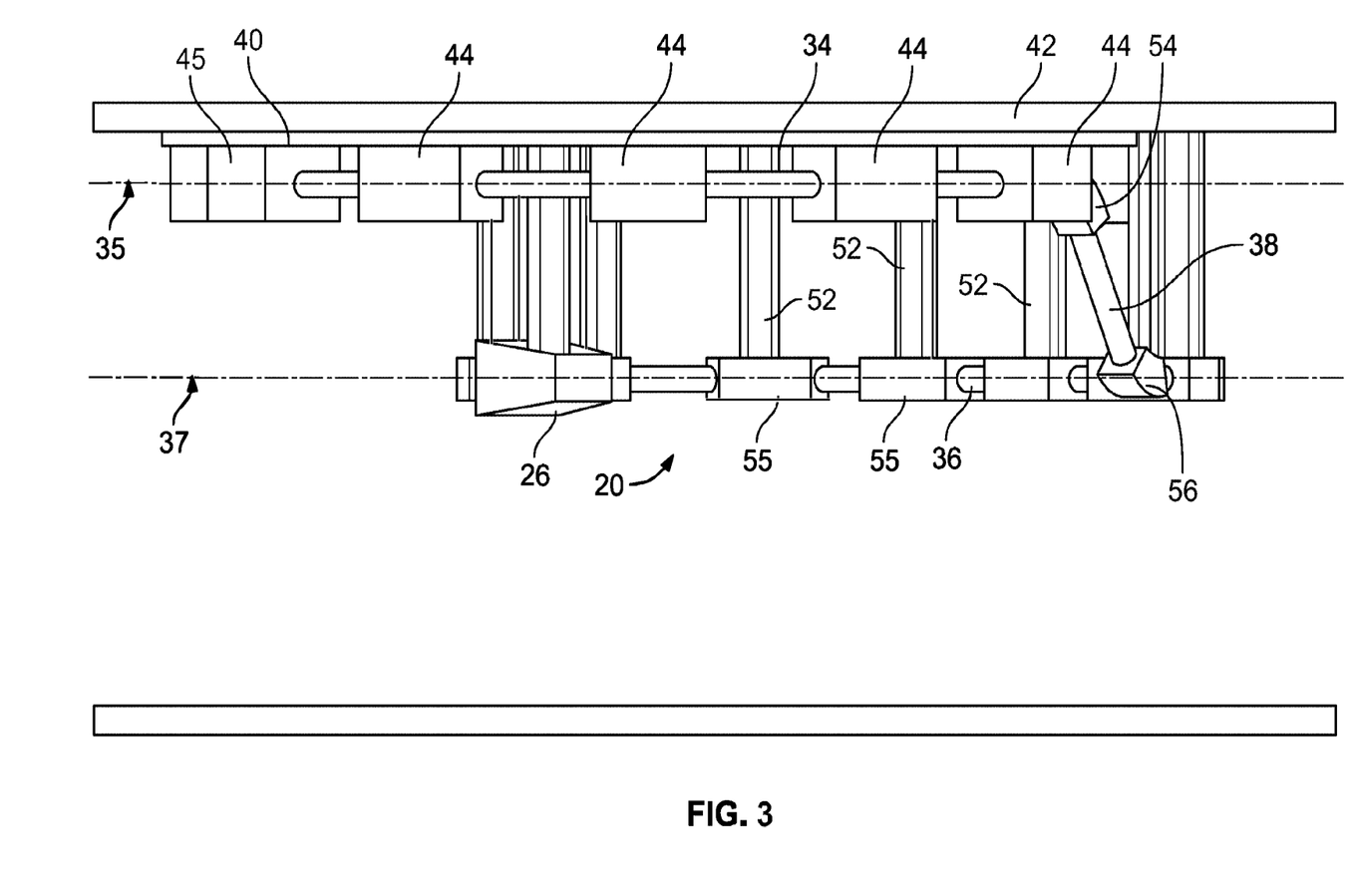
FIG. 3 is a front view of the particle therapy system of FIG. 1 mounted to a ceiling of a room.
Figure 4A:
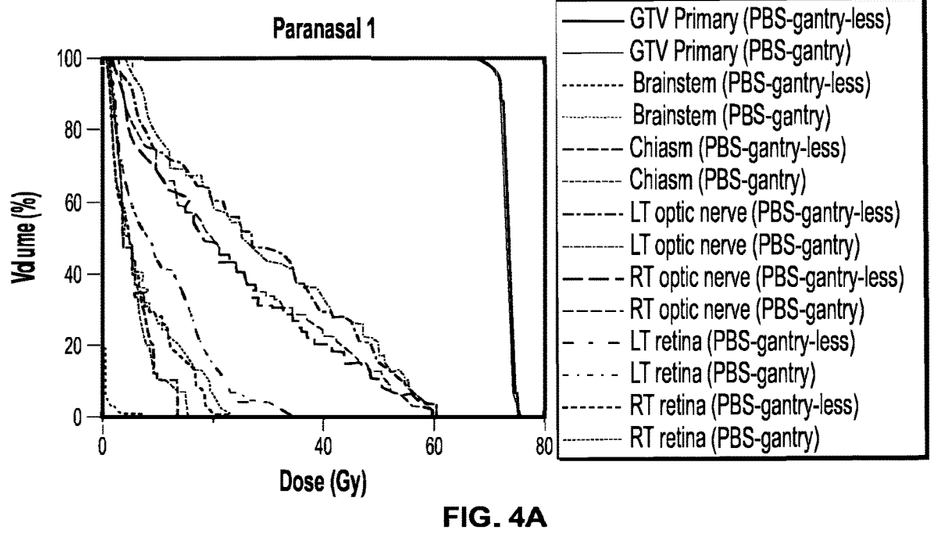
FIG. 4A shows dose volume histograms ("DVHs") for a simulated treatment of a paranasal tumor using an embodiment of a particle therapy system according to the disclosure compared to the same type of treatment performed using a gantry-based particle therapy system (dashed lines).
Figure 4B:
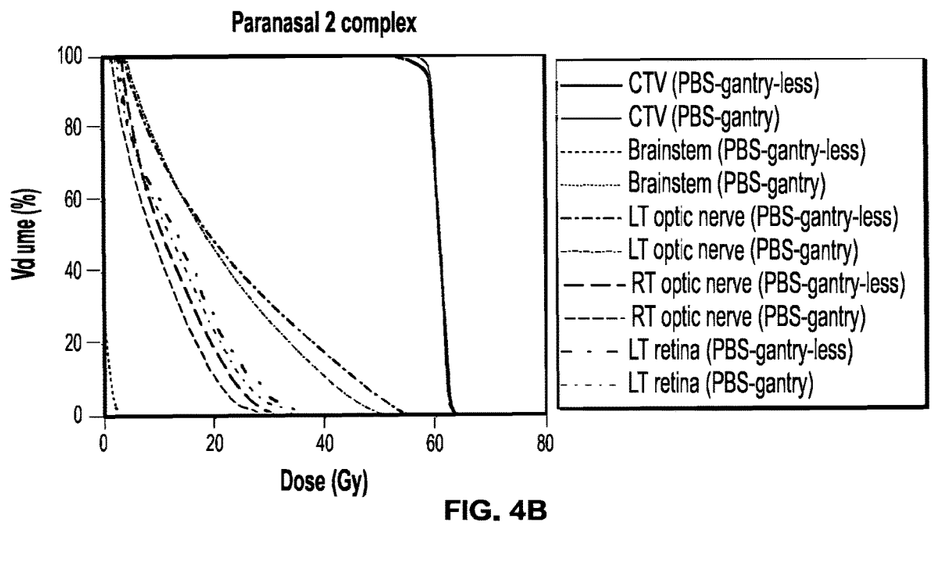
FIG. 4B shows DVHs for another simulated treatment of a paranasal tumor using an embodiment of a particle therapy system according to the disclosure compared to the same type of treatment performed using a gantry-based particle therapy system (dashed lines).
Figure 4C:
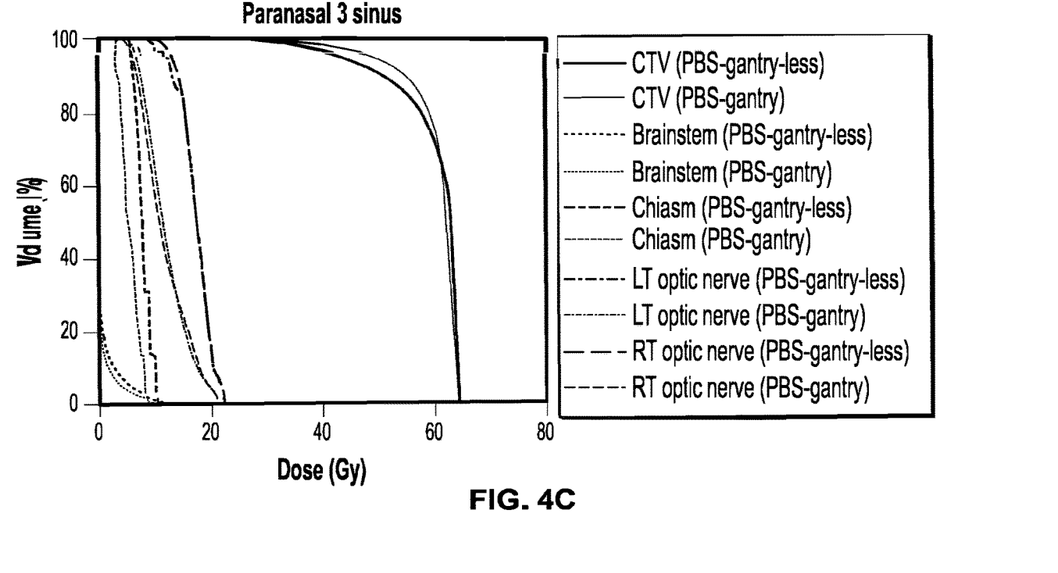
FIG. 4C shows DVHs for another simulated treatment of a paranasal tumor using an embodiment of a particle therapy system according to the disclosure compared to the same type of treatment performed using a gantry-based particle therapy system (dashed lines).
Figure 4D:
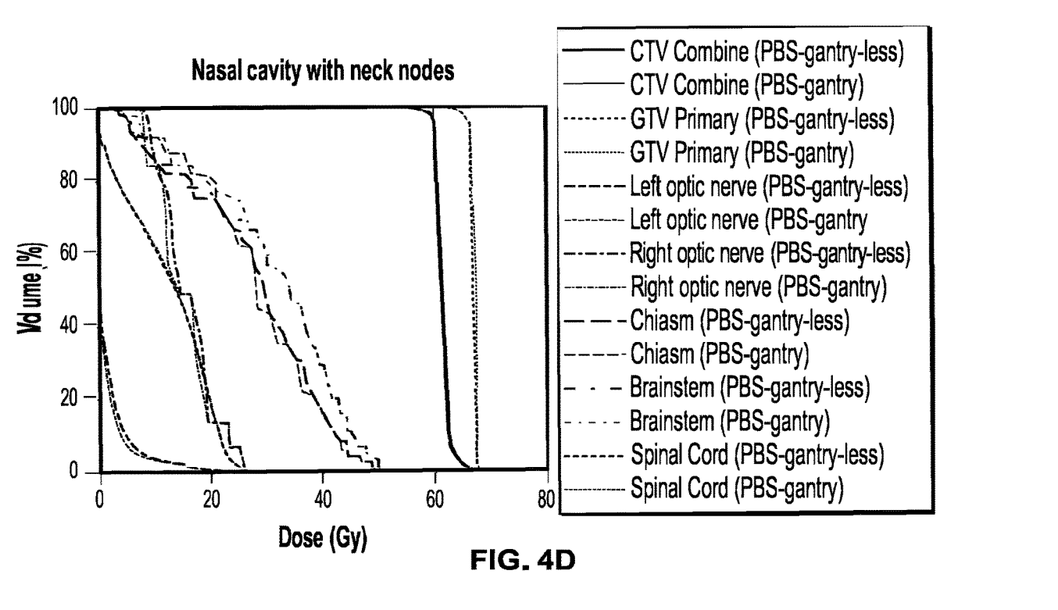
FIG. 4D shows DVHs for another simulated treatment of a nasal cavity tumor with neck nodes using an embodiment of a particle therapy system according to the disclosure compared to the same type of treatment performed using a gantry-based particle therapy system (dashed lines).
Figure 4E:
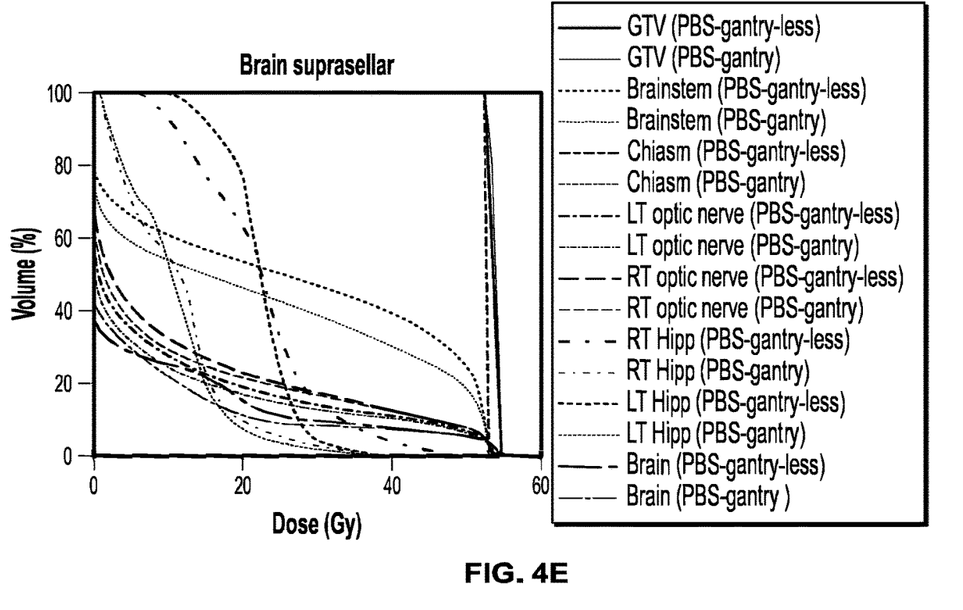
FIG. 4E shows DVHs for another simulated treatment of a suprasellar brain tumor using an embodiment of a particle therapy system according to the disclosure compared to the same type of treatment performed using a gantry-based particle therapy system (dashed lines).
Figure 4F:
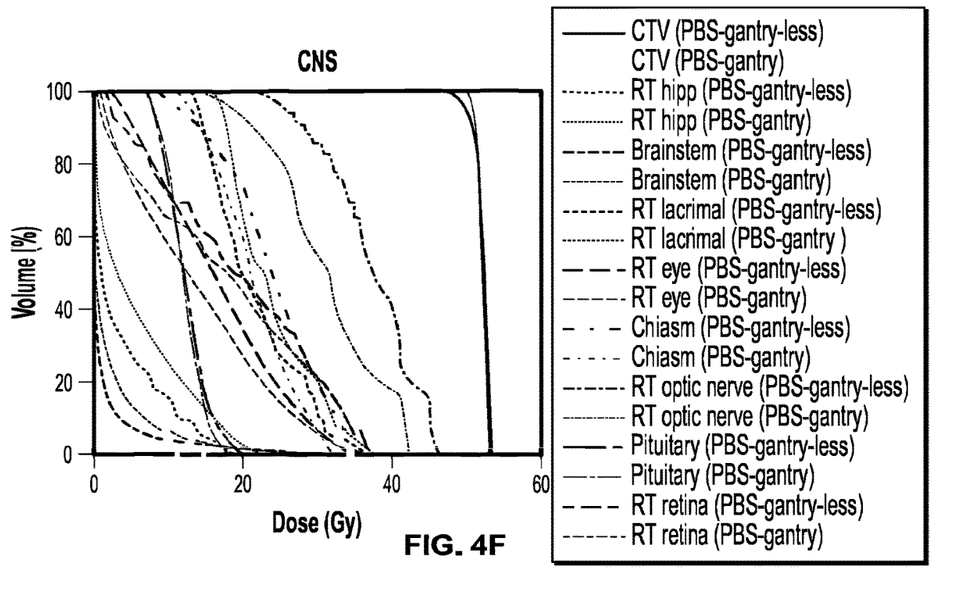
FIG. 4F shows DVHs for another simulated treatment of a central nervous system tumor using an embodiment of a particle therapy system according to the disclosure compared to the same type of treatment performed using a gantry-based particle therapy system (dashed lines).
Figure 4G:
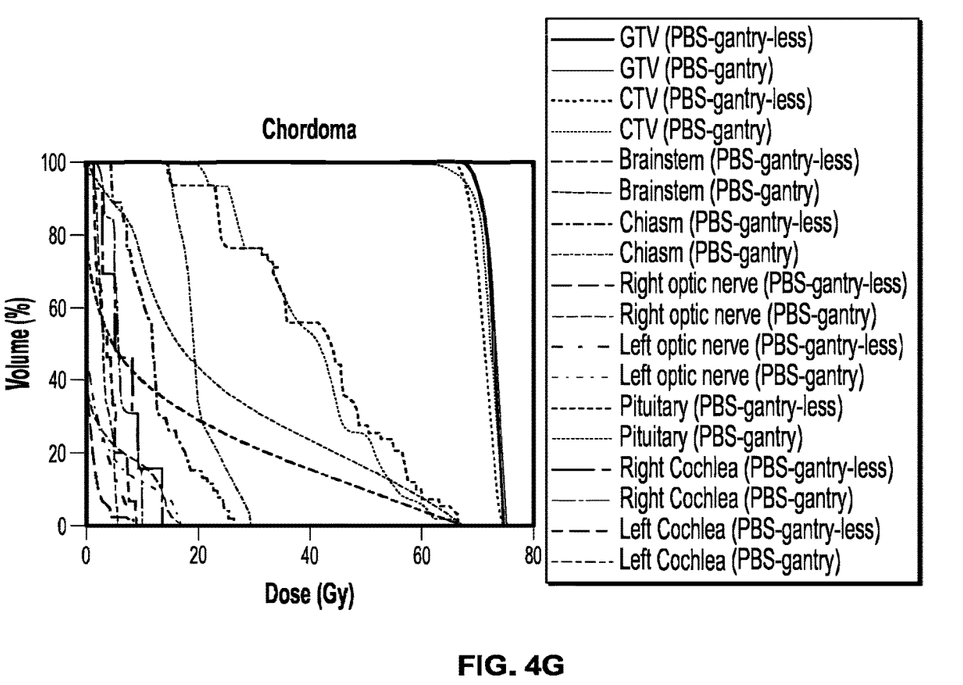
FIG. 4G shows DVHs for another simulated treatment of a chordoma using an embodiment of a particle therapy system according to the disclosure compared to the same type of treatment performed using a gantry-based particle therapy system (dashed lines).

FIGS. 1-3 illustrate non-limiting examples of a particle therapy system 20 according to the present disclosure. The particle therapy system 20 includes, generally, a charged particle generating system 22 that generates an ion beam, a beam transport system 24 to focus and direct the ion beam, and a beam delivery device 26 to direct charged particles in the ion beam toward a patient for treatment. The particle therapy system 20 can operate using a variety of particles, including protons and heavier composite particles, which are used to then treat various types of cancers that may be present within a patient. The particle therapy system 20 can be used to perform proton therapy and heavy ion therapy, for example. In some non-limiting examples, the particle therapy system 20 is a proton beam therapy system.

The charged particle generating system 22 energizes particles, which can then be transported rapidly toward and into a patient to treat a variety of medical conditions, including many types of cancers. In some embodiments, the charged particle generating system 22 can include a particle energizer in the form of an ion source 28, which can be used to produce positively (or negatively) charged particles. In such embodiments, a gas source can feed gas (e.g., pure hydrogen) into the ion source 28, where the electrons in the gas molecules can be removed. The ion source 28 can strip the gas molecules of electrons using lasers, catalysts, radiation, or other suitable ionization techniques to produce positively charged particles. As one example, the ion source 28 may include a linear accelerator. As another example, the ion source 28 may include an electron cyclotron resonance ("ECR") ion source.

An injector 30 can be coupled to the ion source 28 to inject charged particles into the beam transport system 24. The injector 30 may include, for example, a combination of septa and kicker magnets. The septa may be electrostatic or magnetic. The injector 30 can be configured to provide single-turn (e.g., fast) injection, multi-turn injection, charge-exchange injection, and so on. Hydrogen or carbon ions, for example, can be generated in the ion source 28 and passed into the injector 30, which accelerates the ions to form an ion beam (i.e., a charged particle beam). The injector 30 then directs the ion beam into the beam transport system 24, where the ion beam can be further energized and eventually directed toward a patient.

The beam transport system 24 can be coupled to the charged particle generating system 22, and can receive and direct the charged particles (e.g., the ion beam) outwardly away from the injector 30 and ion source 28. The beam transport system 24 can include a beam tube 32, which defines a beam track extending therethrough. For instance, the beam tube 32 can be a metal pipe that is evacuated to a vacuum. Alternatively, the beam tube 32 can include sections or air or helium contained therein. Magnets 44 can be positioned about the beam tube 32 to energize ion beams (e.g., by accelerating or heating the ions or charged particles), bend ion beams, and focus ion beams as they pass along the beam track.

The beam transport system 24, and thus the beam tube 32, can include three distinct segments that together define the beam track. Specifically, the beam track can include an energizing segment 34 formed in a first plane 35, an extracting segment 36 formed in a second plane 37 away from the first plane 35, and a transition segment 38 extending away from the energizing segment 34 toward the extracting segment 36. As will be described, the energizing segment 34 generally circumscribes, or otherwise extends around, a volume to which the ion beam will be delivered by the beam delivery device 26. The extracting segment 36 terminates at a terminal end 39, at which the beam delivery device 26 is coupled. In operation, an ion beam is delivered to the energizing segment 34 from the charged particle generating system 22, where it is delivered to the extracting segment 36 via the transition segment 38.

As shown in FIG. 1, the energizing segment 34 can be positioned upon a platform 40 proximate a mounting surface 42 (e.g., a floor, as shown in FIG. 1, a ceiling, as shown in FIG. 3, or a side wall of a room), and can extend approximately parallel to the mounting surface 42. The extracting segment 36 can be positioned away from the energizing segment 34, and can also extend approximately parallel to the mounting surface 42. In some non-limiting examples, the extracting segment 36 is positioned further away, axially, from the mounting surface 42 than the energizing segment 34.

The energizing segment 34 can be an accelerator. For example, the energizing segment 34 can be a synchrotron having a substantially annular shape and defining a substantially circular outer perimeter. One or more radio frequency (RF) acceleration cavities 45 can be formed in the energizing segment 34 as well. The RF acceleration cavity 45 can include an RF applying electrode that is disposed on the circulating orbit of the accelerator and an RF power source that is in electrical communication with the RF applying electrode by way of a switch. In some aspects, one or more stacked ferrite components can be used to produce an electric field within the energizing segment 34 to accelerate particles therein.

The substantially annular shape of the energizing segment 34 can be defined by a radius of between about 2 meters and about 8 meters, for example. In some non-limiting examples, the energizing segment 34 is defined by a radius of about 3 meters. The beam tube 32, along with the RF acceleration cavity 45 and magnets 44, can define a treatment area 46 formed inwardly from the beam track. Accordingly, the energizing segment 34 circumscribes or otherwise surrounds a volume containing the treatment area 46, unlike gantry-based particle therapy systems where the synchrotron or cyclotron is located remotely (e.g., in a separate room) from the treatment area. In some instances, the energizing segment 34 circumscribes a treatment isocenter. A patient positioner 48 can be situated within the treatment area 46. The patient positioner 48 can orient a patient relative to the beam delivery device 26, which can further allow the beam delivery device 26 to effectively supply an ion beam to different areas of the patient (e.g., the head or the stomach) to treat different types of medical conditions. In some non-limiting examples, an imaging device 50 can also be positioned within the treatment area 46. The imaging device 50 can be used for imaging or locating the treatment target (e.g., a tumor) within a patient on the patient positioner 48. The imaging device 50 can be an X-ray machine or a CT scanner, for example. By placing the treatment area 46 inward from the beam track, the footprint of the particle therapy system 20 is reduced significantly. For example, the entire particle therapy system 20 can be stored and operated within the same room. As one example, the entire particle therapy system 20 can be contained within a 50 m$^2$ room.

In use, the energizing segment 34 is supplied with an ion beam from the injector 30. If the energizing segment 34 is designed as a synchrotron, magnets 44 (e.g., quadrupole and dipole magnets) can be positioned about the beam tube 32 to steer the ion beam about the energizing segment 34 a number of times so that the ion beam repeatedly passes through the RF acceleration cavity 45, which increases the energy of the ion beam. Once the energy of the ion beam traveling in the energizing segment 34 has reached a preselected, desired energy level (e.g., 100-300 MeV), the ion beam can be extracted from the energizing segment 34 into the transition segment 38. Extraction may occur by way of bumping or kicking the ion beam to an outer trajectory so that it passes through a septum, or by way of resonance extraction.

The transition segment 38 can extend tangentially and angularly away from the energizing segment 34 to direct the ion beam out of the plane (e.g., the first plane 35) of the energizing segment 34, to the elevation of the patient within the treatment area 46 (e.g., the elevation of the second plane 37). In some non-limiting examples, the transition segment 38 angles obtusely away from the energizing segment 34 to form an angle of between about 100 degrees and about 170 degrees with respect to the first plane 35, which includes the energizing segment 34. As shown in FIG. 1, the transition segment 38 extends upwardly away from the first plane 35 at an angle of between about 115 degrees and about 155 degrees.

Alternatively, the first plane 35 and the second plane 37 can be coplanar, as shown in FIG. 2. The extracting segment 136 can extend arcuately and radially inward from the energizing segment 34 into the treatment area 46 and toward the patient positioner 48 and the imaging device 50. A plurality of magnets 55 can direct and focus the ion beam as it passes into the beam delivery device 26 and toward a patient, as described below. In these aspects, the transition segment 38 can extend inwardly away from the energizing segment 34 within the same plane as the extracting segment 136. In some aspects, the transition 38 is omitted from the beam tube 32 entirely. In still other aspects, the first plane 35 and the second plane 37 can be oriented approximately perpendicular to one another. In some non-limiting examples, the first plane 35 is obliquely oriented (e.g., oriented nonparallel) with the second plane 37. Optionally, the extracting segment 136 can be provided with a helical shape that extends along multiple planes.

The transition segment 38 can guide a highly energized ion beam from the energizing segment 34 into the extracting segment 36, which can reside in the second plane 37 away from the first plane 35. The extracting segment 36 can have an arcuate shape that extends, initially, outward beyond the circular outer perimeter of the energizing segment 34. The extracting segment 36 can then spiral inwardly within the second plane 37, such that the beam track extends back inside the circular outer perimeter of the energizing segment 34, toward the treatment area 46 and the patient positioner 48 received inwardly from the energizing segment 34. The beam delivery device 26 can be coupled to the extracting segment 36, which can be positioned inward from the outer perimeter of the energizing segment 34, within the treatment area 46. In some non-limiting examples, legs 52 can extend away from the extracting segment 36 to help support the extracting segment 36 upon the mounting surface 42 or the platform 40. The legs 52 can extend perpendicularly between the platform 40 and the extracting segment 36, and can be coupled to the mounting surface 42 or platform 40 using fasteners, adhesives, or other mechanical couplings, for example.

The extracting segment 36 can direct highly energized ion beams from the transition segment 38 into the beam delivery device 26 using one or more magnets. For example, the beam transport system 24 can include a plurality of magnets 55 (e.g., focusing magnets and steering magnets), which direct, energize, and shape the ion beam as it passes through the beam transport system 24 toward the beam delivery device 26. As an example, the magnets 55 can include focusing magnets that are quadrupole magnets, and steering magnets that are dipole magnets. The magnets 55 are used to contain the ion beam within the beam track and to deliver the ion beam to the beam delivery device 26 that is situated within the treatment area 46. In some non-limiting examples, a magnetic system of dipoles, quadrupoles, sextupoles, octupoles, multipoles, or combinations of some or all of these magnet types can be used to both focus and direct highly energized ion beams toward the treatment area 46. The placement and parameters (e.g., strength, number of magnetic poles) of the magnets 55 are designed to capture, with high efficiency, an ion beam extracted from the energizing segment 34. Although specific magnetic system layouts that can direct ion beams effectively along the beam track are described, the magnetic systems can be optimized to include more or less magnets of varying polarity and strength to retrofit the particle therapy system 20 for a room within a hospital. In the examples provided, the particle therapy system 20 has been adapted to fit in a room conventionally used to house a linear accelerator ("LINAC") treatment system, within an area of about 7 meters by 7 meters.

With specific reference to FIG. 2, a specific combination of magnets 55 kept at room temperature or superconducting temperature can be used to extract and bend an ion beam toward the beam delivery device 26 and treatment area 46. Although FIG. 2 shows one example configuration for the magnets 55 in the extracting segment 36, it will be appreciated by those skilled in the art that different configurations of magnets 55 along the beam tube 32 in the extracting segment 36 can be used depending on the geometries involved with the particular installation of the particle therapy system 20. The ion beam can be first extracted from the energizing segment 34 using two superconducting dipole magnets 54, 56, which are positioned within the transition segment 38. The superconducting dipole magnets 54, 56 can bend the ion beam angularly away (e.g., upward in FIG. 1, downward in FIG. 3, or sideways, depending on the orientation of the particle therapy system 20) from the energizing segment 34 and out of plane (i.e., the first plane 35) from the energizing segment 34. In some non-limiting examples, the beam is bent upward at an angle of about 45 degrees. The two superconducting dipole magnets 54, 56 direct the ion beam to the extracting segment 36.

The extracting segment 36 can include a number of magnets bending magnets, such as ten (as well as additional focusing magnets), for example, which are positioned about the second plane 37 to transport ion beams to a position of about 2 meters away from the patient positioner 48 within the treatment area 46. In this particular and non-limiting example, after being directed out of plane from the energizing segment 34 and through the transition segment 38, the ion beam passes through a beam drift tube 58 of about 0.6 meters before passing through a first dipole magnet 60. The first dipole magnet 60 can have a 0.6 meter dipole length that produces a 1.06 T magnetic field to bend the ion beam about 15 degrees. Next, the ion beam passes through another 0.7 meter beam drift tube 62, which can also include an ion beam focusing quadrupole magnet 64. The ion beam is then transported to a second dipole magnet 66, which has a 0.6 m dipole length and produces a 0.71 T magnetic field to bend the ion beam by about 10 degrees. The second dipole magnet 66 can also include pole phase rotation. The ion beam can then pass through another 0.7 meter beam drift tube 68 having another focusing quadrupole magnet 70, to a third dipole magnet 72. Like the second dipole magnet 66, the third dipole magnet 72 can have pole phase rotation, as well as a dipole length of 0.6 meters that produces a 0.71 T magnetic field to bend the ion beam by about 10 degrees. Another beam drift 74 of 0.6 meters extends from the third dipole magnet 72, and includes a focusing quadrupole magnet 76 as well.

The ion beam then passes towards fourth and fifth dipole magnets 78, 84 having similar characteristics, and which are spaced apart from one another by a 0.6 m beam drift tube 80 that can include a focusing quadrupole magnet 82. The fourth and fifth dipole magnets 78, 84 each have a 0.6 meter dipole length and each produce a 1.75 T magnetic field to separately bend the beam 25 degrees. A beam drift tube 86 of about 0.9 meters extends away from the fifth dipole magnet 84, and can include two focusing quadrupole magnets 88, 90. A sixth dipole magnet 92 having a 0.5 meter dipole length and producing a 0.85 T magnetic field is positioned away from the beam drift tube 86. The sixth dipole magnet 92 can include pole phase rotation, and can bend the ion beam by about 10 degrees. The ion beam then passes through another beam drift 94 of 0.5 meters having a focusing quadrupole magnet 96, to a seventh dipole magnet 98. The seventh dipole magnet 98 bends the ion beam by about 8 degrees, and has a 0.6 meter dipole length used to produce a magnetic field of 0.57 T. Again, the seventh dipole magnet 98 can have pole phase rotation. A beam drift 100 of 0.3 meters having a focusing quadrupole magnet 102 extends from the seventh dipole magnet 98 toward the eighth dipole magnet 104.

In the example shown in FIG. 2, the eighth and ninth dipole magnets 104, 108 have similar characteristics, and are spaced apart from one another by a beam drift tube 106 of 0.3 meters. The eighth and ninth dipole magnets 104, 108 each have a 0.7 meter dipole length, and can each produce a magnetic field of 2.66 T. In some non-limiting examples, the eighth and ninth dipole magnets 104, 108 are cryogenically cooled to superconducting temperatures, and act as superconductors. The eighth and ninth dipole magnets 104, 108 can each bend the ion beam by about 45 degrees. A final beam drift tube 110 of about 0.4 meters extends away from the ninth dipole magnet 108 toward a tenth dipole magnet 112. The tenth dipole magnet 112 can include pole phase rotation and can have a dipole length of 0.6 meters. The tenth dipole magnet 112 can produce a magnetic field of about 1.75 T, which bends the ion beam by about 25 degrees.

Once the ion beam has passed beyond the tenth dipole magnet 112, it can be directed to the beam delivery device 26 coupled to the extracting segment 36 of the beam track. The beam delivery device 26 can extend inwardly into the treatment area 46 defined within the annular shape of the energizing segment 34, and can act as a nozzle to direct a beam either in plane or at an angle relative to the plane in which the extracting segment 36 of the beam track is arranged (i.e., the second plane 37).

The beam delivery device 26 is designed to deliver precise dose distributions to a target volume within a patient. The beam delivery device 26 can include components that may either modify or monitor specific properties of an ion beam in accordance with a treatment plan. In some instances, the beam delivery device 26 provides for pencil beam scanning of the ion beam. The beam delivery device 26 can include a beam spreading device to spread or otherwise modify the ion beam position and profile, a dispersive element to modify the ion beam energy, and/or a plurality of beam sensors to monitor such properties. The beam spreading device can transform the beam from the energizing segment 34 and the extracting segment 36 into a beam that is suitable for patient treatment. In some non-limiting examples, the beam spreading device can bend the beam up or down (or right or left) by about 15 degrees, which helps create different treatment angles for patients. Mechanical or magnetic elements can be used to spread the beam to the appropriate shape (e.g., to conform to the patient target), for example. In some aspects, the beam delivery device 26 can include a range shifter. In some non-limiting examples, the beam delivery device 26 can magnetically scan the ion beam and can provide pencil beam scanning for patient treatment.

As an example, the beam delivery device 26 can include a nozzle at which the beam tube 32 terminates. The nozzle generally includes an end through which the ion beam exits and is directed towards the patient. As noted, the nozzle can include components that can shape, steer, or otherwise modify or modulate the ion beam. For instance, the nozzle can include scanning electromagnets (e.g., wobbler magnets), a scatterer, a range shifter, a collimator (e.g., a multi-leaf collimator), a ridge filter, and so on.

The particle therapy system 20 can be controlled by a central controller that includes a processor 114 and a memory 116 in communication with the processor 114. A beam track controller 118 is in communication with the processor 114 and is configured to control operational parameters of the charged particle generating system 22, the energizing segment 34, and the extracting segment 36 of the beam track. A positioner controller 120 can be in electrical communication with the processor 114, and can be used to control the position and orientation of the patient positioner 48 within the treatment area 46. A scanning controller 122 can be in communication with the processor 114 to control the beam delivery device 26. An imaging controller 124 can be in communication with the processor 114 as well, to control the imaging device 50. The memory 116 can store treatment plans prescribed by a treatment planning system 126 that is in communication with the processor 114 and the memory 116, as well as control parameters or instructions to be delivered to the beam track controller 118, the positioner controller 120, the imaging controller 124, and/or the scanning controller 122. The memory 116 may also store relevant patient information that can be accessed during a treatment session.

Using the combination of features described above, the particle therapy system 20 has been simulated to effectively treat tumors in patients regardless of location. Using the scanning beam delivery modality (e.g., pencil beam scanning) incorporated by the beam delivery device 26, optimal combinations of beam-to-patient geometries can be achieved without a gantry. Further, effective treatments can be achieved by the particle therapy system 20, which is much smaller, more compact, and less expensive than conventional gantry-based systems currently being used to perform particle therapy. By locating the treatment area inside the outer perimeter of the beam track, substantial space is saved.

Various different treatment processes were simulated both using the particle therapy system 20 and compared to simulation using a proton therapy system incorporating a gantry. Based on the results presented in FIGS. 4A-4G, the particle therapy system 20 proved as or nearly as effective as the proton therapy system incorporating a gantry in nearly every treatment simulation performed. As shown in FIGS. 4A-4G, target dose levels can be delivered to various different tumor types using the gantry-less particle therapy system described in the present disclosure. The gantry-less system is thus able to deliver the same dose to the treatment volumes, while in some instance reducing the dose delivered to organs-at-risk.

Within this specification embodiments have been described in a way which enables a clear and concise specification to be written, but it is intended and will be appreciated that embodiments may be variously combined or separated without parting from the invention. For example, it will be appreciated that all preferred features described herein are applicable to all aspects of the invention described herein.

Thus, while the invention has been described in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein.

Various features and advantages of the invention are set forth in the following claims.

We claim:

1. A particle therapy system for treating a patient, comprising:
   a charged particle generating system comprising:
      an ion source;
      an injector that injects an ion beam from the ion source into a beam track;
   a beam transport system defining the beam track and coupled to the charged particle generating system, the beam transport system comprising:
      a beam tube evacuated to a vacuum and defining the beam track, the beam tube comprising an energizing segment extending in a first plane and circumscribing a volume to which the ion beam is to be delivered, an extracting segment extending in a second plane that is away from the first plane and terminating at a terminal end, and a transition segment that connects the energizing segment to the extracting segment, wherein the ion beam is received in the energizing segment from the injector;
      a plurality of magnets that adjust a trajectory of the ion beam in the beam tube as the ion beam passes through each of the plurality of magnets;
      an acceleration cavity that accelerates the ion beam as the ion beam passes through the acceleration cavity;
   a beam delivery device coupled to the terminal end of the extracting segment and positioned inward from an outer perimeter of the energizing segment, the beam delivery device configured to direct the ion beam from the extracting segment toward a treatment area in the volume circumscribed by the energizing segment, and wherein the first plane is parallel to the second plane.

2. The system of claim 1, wherein the first plane and the second plane are spaced apart from one another, and the transition segment is angled away from the first plane toward the second plane.

3. The system of claim 2, wherein the transition segment extends tangentially away from the energizing segment toward the extracting segment.

4. The system of claim 1, wherein the energizing segment is defined by a substantially circular outer perimeter.

5. A particle therapy system for treating a patient, comprising:
a charged particle generating system comprising:
an ion source;
an injector that injects an ion beam from the ion source into a beam track;
a beam transport system defining the beam track and coupled to the charged particle generating system, the beam transport system comprising:
a beam tube evacuated to a vacuum and defining the beam track, the beam tube comprising an energizing segment extending in a first plane and circumscribing a volume to which the ion beam is to be delivered, an extracting segment extending in a second plane that is away from the first plane and terminating at a terminal end, and a transition segment that connects the energizing segment to the extracting segment, wherein the ion beam is received in the energizing segment from the injector;
a plurality of magnets that adjust a trajectory of the ion beam in the beam tube as the ion beam passes through each of the plurality of magnets;
an acceleration cavity that accelerates the ion beam as the ion beam passes through the acceleration cavity;
a beam delivery device coupled to the terminal end of the extracting segment and positioned inward from an outer perimeter of the energizing segment, the beam delivery device configured to direct the ion beam from the extracting segment toward a treatment area in the volume circumscribed by the energizing segment;
wherein the energizing segment is defined by a substantially circular out perimeter; and
wherein the extracting segment has an arcuate shape.

6. The system of claim 5, wherein the arcuate shape spirals radially inwardly toward the volume circumscribed by the energizing segment.

7. The system of claim 1, wherein legs extend away from the extracting segment toward the first plane to support the extracting segment.

8. The system of claim 1, wherein the beam delivery device includes a nozzle comprising scanning electromagnets that provide pencil beam scanning of the ion beam.

9. The system of claim 1, wherein the plurality of magnets comprises a plurality of bending magnets and a plurality of focusing magnets.

10. The system of claim 1, wherein the plurality of magnets includes dipole magnets and quadrupole magnets.

11. A particle therapy system for treating a patient, comprising:
a charged particle generating system comprising:
an ion source;
an injector that injects an ion beam from the ion source into a beam track;
a beam transport system defining the beam track and coupled to the charged particle generating system, the beam transport system comprising:
a beam tube evacuated to a vacuum and defining the beam track, the beam tube comprising an energizing segment extending in a first plane and circumscribing a volume to which the ion beam is to be delivered, an extracting segment extending in a second plane that is away from the first plane and terminating at a terminal end, and a transition segment that connects the energizing segment to the extracting segment, wherein the ion beam is received in the energizing segment from the injector;
a plurality of magnets that adjust a trajectory of the ion beam in the beam tube as the ion beam passes through each of the plurality of magnets;
an acceleration cavity that accelerates the ion beam as the ion beam passes through the acceleration cavity;
a beam delivery device coupled to the terminal end of the extracting segment and positioned inward from an outer perimeter of the energizing segment, the beam delivery device configured to direct the ion beam from the extracting segment toward a treatment area in the volume circumscribed by the energizing segment, and
wherein the energizing segment comprises one of a synchrotron or a cyclotron.

12. The system of claim 1, further comprising a patient positioner situated inward from the outer perimeter.

13. A particle therapy system for treating a patient, comprising:
an ion source;
an injector that extracts an ion beam from the ion source;
a beam tube coupled to the injector to receive the ion beam from the injector, the beam tube defining a beam track that includes an annular portion circumscribing a volume and an arcuate portion in fluid communication with the annular portion and extending at least partially inward from the annular portion;
a beam delivery device coupled to the arcuate portion and extending radially inward from the annular portion of the beam track into a patient treatment area contained in the volume circumscribed by the annular portion;
wherein a transition portion is formed between the annular portion and the arcuate portion and is in fluid communication with the annular portion and the arcuate portion to direct the ion beam from the annular portion toward the arcuate portion;
wherein the annular portion extends in a first plane and the arcuate portion extends in a second plane different from the first plane; and
wherein the first plane and the second plane are approximately perpendicular to one another.

14. The particle therapy system of claim 13, wherein the arcuate portion extends radially inward away from the annular portion in a plane approximately coplanar with the annular portion.

15. The particle therapy system of claim 13, wherein a transition portion is formed between the annular portion and the arcuate portion and is in fluid communication with the annular portion and the arcuate portion to direct the ion beam from the annular portion toward the arcuate portion.

16. The particle therapy system of claim 15, wherein the annular portion extends in a first plane and the arcuate portion extends in a second plane different from the first plane.

17. The particle therapy system of claim 16, wherein the first plane and the second plane are approximately perpendicular to one another.

18. The particle therapy system of claim 16, wherein the first plane is obliquely oriented with the second plane.

19. A particle therapy system for treating a patient, comprising:
- an ion source;
- an injector that extracts an ion beam from the ion source;
- a beam tube coupled to the injector to receive the ion beam from the injector, the beam tube defining a beam track that includes an annular portion circumscribing a volume and an arcuate portion in fluid communication with the annular portion and extending at least partially inward from the annular portion;
- a beam delivery device coupled to the arcuate portion and extending radially inward from the annular portion of the beam track into a patient treatment area contained in the volume circumscribed by the annular portion;
- wherein a transition portion is formed between the annular portion and the arcuate portion and is in fluid communication with the annular portion and the arcuate portion to direct the ion beam from the annular portion toward the arcuate portion;
- wherein the annular portion extends in a first plane and the arcuate portion extends in a second plane different from the first plane; and
- wherein the first plane and the second plane are approximately parallel to one another.

20. The particle therapy system of claim 19, wherein the first plane and the second plane are spaced apart from one another.

\* \* \* \* \*

UNITED STATES PATENT AND TRADEMARK OFFICE
CERTIFICATE OF CORRECTION

PATENT NO. : 11,350,516 B2
APPLICATION NO. : 17/090809
DATED : May 31, 2022
INVENTOR(S) : Thomas Bortfeld et al.

It is certified that error appears in the above-identified patent and that said Letters Patent is hereby corrected as shown below:

In the Claims

Column 11, Claim 5, Line 41, "out" should be --outer--.

Signed and Sealed this
Sixteenth Day of August, 2022

Katherine Kelly Vidal
*Director of the United States Patent and Trademark Office*